United States Patent [19]

Zaiger

[11] Plant 4,106

[45] Sept. 20, 1977

[54] NECTARINE TREE

[76] Inventor: Chris Floyd Zaiger, 537 Rosemore Ave., Modesto, Calif. 95351

[21] Appl. No.: 709,613

[22] Filed: July 28, 1976

[51] Int. Cl.[2] ..... A01H 5/03

[52] U.S. Cl. ..... Plt./41

[58] Field of Search ..... Plt./41

*Primary Examiner*—Robert E. Bagwill

[57] ABSTRACT

A variety of nectarine tree which is large size, vigorous, dense growth; the tree being a productive and regular bearer of medium size, early ripening, clingstone fruit having firm yellow flesh and a high degree of red skin color.

1 Drawing Figure

ORIGIN OF VARIETY

The new variety of nectarine was originated in my experimental orchard at Modesto, Calif. It was selected from a second generation seedling between Sun Grand Nectarine (U.S. Plant Pat. No. 974) and a Peach seedling of the parentage, (Sun Grand Nectarine × Merill Gem Peach (U.S. Plant Pat. No. 868).

ASEXUAL REPRODUCTION OF THE VARIETY

Asexual reproduction of the variety was accomplished by budding and grafting, as performed at Modesto, Calif., shows that said characteristics come true to form and are established and transmitted through succeeding propagations.

SUMMARY OF THE VARIETY

My new invention relates to a new and distinct variety of nectarine tree which bears yellow-fleshed clingstone fruit characterized as to novelty by early ripening. The ripening period being approximately 8 days earlier than Zee Gold Nectarine (U.S. Plant Pat. No. 3,087), and having an exceptional high degree of red skin color. The fruit is further characterized by being firm, with good shipping and handling qualities. The high degree of red color, firm fruit, fills the need of this early period for a high quality nectarine that will ship long distances.

DESCRIPTION OF THE PHOTOS

The accompanying photographs show typical specimens of the foliage and fruit of my new variety, with upper and lower surfaces of the foliage being illustrated and exterior and a sectional view of the fruit being shown. These illustrations were taken shortly after being picked at maturity (shipping ripe). The colors are as nearly true as is reasonably possible in color representation of this type.

DESCRIPTION OF THE VARIETY

The following is a detailed description of the foliage and fruit of my new variety, as based upon observation of specimens grown at Modesto, Calif., with color terminology in accordance with Reinhold Color Atlas by A. Kornerup and J. H. Wanscher.

Tree:
- *Size.*—Large.
- *Vigor.*—Vigorous.
- *Density.*—Dense.
- *Form.*—Spreading.
- *Production.*—Productive.

Trunk:
- *Size.*—Stocky to medium.

- *Surface.*—Medium shaggy.
- *Color.*—Brownish gray.

Branches:
- *Size.*—Medium stocky.
- *Surface.*—Medium shaggy.
- *Color.*—Brown to greyish brown.
- *Lenticels.*—Medium quantity.

Leaves:
- *Size.*—Large; Mature length 6½" to 8¼"; Width 1½" to 1¾".
- *Texture.*—Smooth.
- *Margin.*—Crenate.
- *Petiole.*—Medium length.
- *Glands.*—Number 2 to 6; Usually 4; Reniform.
- *Color.*—Upper surface — Plate No. (29-E-5) to (29-F-5). Lower surface — Plate No. (29-D-7) to (29-E-7).

Flower buds:
- *Size.*—Medium.
- *Length.*—Medium.

Flowers:
- *Blooming period.*—Feb. 26, 1976 to Mar. 10, 1976.
- *Size.*—Medium, non-showy.
- *Color.*—Pink.
- *Pollen.*—Present.

Fruit:
- *Maturity when described.*—Firm to hard ripe.
- *Date of first picking.*—May 20, 1976.
- *Date of last picking.*—June 1, 1976.
- *Size.*—Uniform, medium. Average diameter axially 2 3/16" to 2 5/16". Average transversely in suture plane 2 3/16" to 2 5/16".
- *Form.*—Uniform; Globose.
- *Suture.*—Distinct, extends from base to apex, with slight depression beyond pistil point.
- *Ventral surface.*—Rounded, lips equal to unequal.
- *Cavity.*—Rounded; circular; Average depth ⅜"; Average breadth ⅞".
- *Base.*—Truncate.
- *Apex.*—Short.

Skin:
- *Thickness.*—Medium.
- *Texture.*—Medium; tenacious to flesh.
- *Tendency to crack.*—None.
- *Down.*—Wanting.
- *Color.*—Yellow ground color (3-A-7 to 4-A-7) almost entirely overspread with red (8-B-8 to 9-B-8).

Flesh:
- *Juice.*—Moderate.
- *Amygdalin.*—Wanting.
- *Texture.*—Medium, meaty.

*Ripens.*—Comparatively even.
*Flavor.*—Subacid.
*Eating quality.*—Good.
*Aroma.*—Very little.
*Color.*—Yellow (4-A-7 to 5-A-7).

Stone:

*Type.*—Clingstone.
*Size.*—Medium; Average length — 1¼"; Average breadth — 1"; Average thickness — ⅝".
*Form.*—Ovoid.
*Base.*—Straight to slightly oblique.
*Apex.*—Acuminate.
*Sides.*—Mostly equal.
*Surface.*—Pitted throughout.
*Ridges.*—Rounded toward apex; Interrupted.
*Dorsal edge.*—Narrow.
*Ventral edge.*—Thin.
*Tendency to split.*—Slight.
*Color.*—Brown (8-C-4 to 8-D-5).

Use:

*Market.*—Local and long distance shipping. Dessert.

Keeping quality: Good.
Shipping quality: Good.

The tree and its fruit herein described may vary in slight detail due to climatic and soil conditions under which the variety may be grown. The description is that of the variety produced under ecological conditions prevailing at Modesto, Calif.

The following is claimed:

1. A new and distinct variety of nectarine tree as illustrated and described which bears medium, clingstone, fruit having yellow flesh; characterized by ripening approximately 10 days earlier than the Zee Gold (U.S. Plant Pat. No. 3,087), and further characterized in comparison with other varieties by early maturing fruit of uniform size with a high degree of red skin color and good long distance shipping quality.

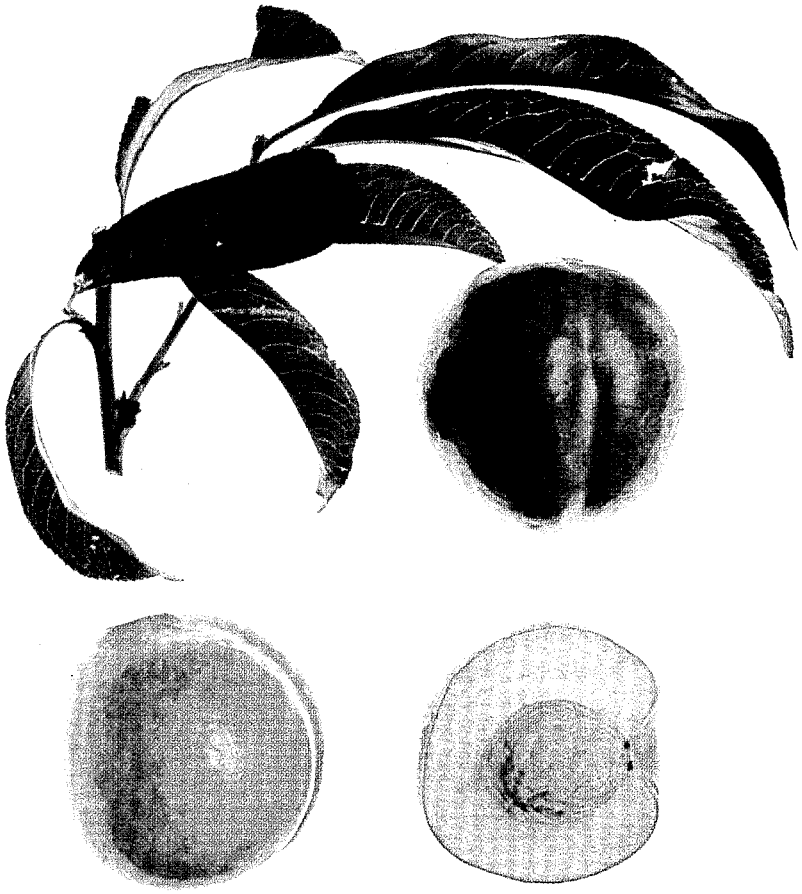

* * * * *